(12) United States Patent
Geroni et al.

(10) Patent No.: US 6,258,786 B1
(45) Date of Patent: Jul. 10, 2001

(54) 13-DIHYDRO-3' AZIRIDINO ANTHRACYCLINES

(75) Inventors: Maria Cristina Geroni; Marina Ripamonti; Michele Caruso; Antonino Suarato, all of Milan (IT)

(73) Assignee: Pharmacia & Upjohn S.p.A., Milan (IT)

( * ) Notice: Subject to any disclaimer, the term of this patent is extended or adjusted under 35 U.S.C. 154(b) by 0 days.

(21) Appl. No.: 09/445,443

(22) PCT Filed: Apr. 9, 1999

(86) PCT No.: PCT/EP99/02567
§ 371 Date: Dec. 13, 1999
§ 102(e) Date: Dec. 13, 1999

(87) PCT Pub. No.: WO99/52921
PCT Pub. Date: Oct. 21, 1999

(30) Foreign Application Priority Data

Apr. 15, 1998 (GB) .................................................. 9808027

(51) Int. Cl.$^7$ ............................. A61K 31/70; C07H 15/24
(52) U.S. Cl. ................................................. 514/34; 536/6.4
(58) Field of Search ...................... 536/6.4, 18.5; 514/34

(56) References Cited

U.S. PATENT DOCUMENTS 4,604,381 * 8/1986 Penco et al. ........................... 514/34
5,532,218 * 7/1996 Bargiotti et al. ....................... 514/34

FOREIGN PATENT DOCUMENTS 0 128 670 A1 * 12/1984 (EP) .

* cited by examiner

Primary Examiner—Elli Peselev
(74) Attorney, Agent, or Firm—Oblon, Spivak, McClelland, Maier & Neustadt, P.C.

(57) ABSTRACT

The present invention relates to anthracycline glycosides, to a process for their preparation and to pharmaceutical compositions containing the same.

10 Claims, No Drawings

13-DIHYDRO-3' AZIRIDINO ANTHRACYCLINES

The invention relates to anthracycline glycosides, to a process for their preparation and to pharmaceutical compositions containing them.

The invention provides anthracycline glycosides having the formula I:

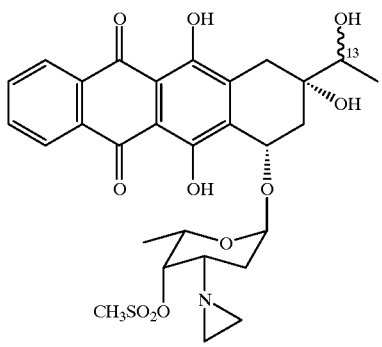

wherein the wavy line means that the hydroxy group at 13-position may be at α or β position, or a mixture thereof. Compounds of formula I comprise derivatives in which the hydroxy group at 13 position has configuration 13(S), 13(R), or a mixture of both 13(R) and 13(S) diastereoisomers, that is:
4-demethoxy-13(S/R)-dihydro-3'-deamino-3'-aziridinyl-4' methansulfonyl daunorubicin (Ia),
4-demethoxy-13(S)-dihydro-3'-deamino-3'-aziridinyl-4'-methansulfonyl daunorubicin (Ib) and
4-demethoxy-13(R)-dihydro-3'-deamino-3'-aziridinyl-4'-methansulfonyl daunorubicin (Ic).

More preferably, the present invention provides anthracycline glycosides having the formula I as above defined characterized in that the 13-carbon atom is S, i.e. 4-demethoxy-13(S)-dihydro-3'-deamino-3'-aziridinyl-4'-methansulfonyl daunorubicin (Ib).

The compounds of the formula I may be prepared by reducing the anthracycline of the formula II

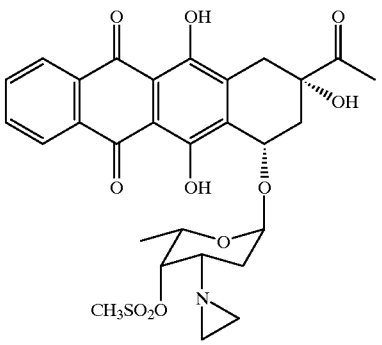

in presence of a reductive agent, such as sodium borohydride, in a mixture of organic solvents, such as methylene chloride and methanol, preferably at a temperature below 50° C., more preferably at −70° C., and, if desired and necessary, by separating the resultant mixture of 13(R) and 13(S) compounds into the single diastereoisomer. For example, the single 13-dihydro diastereoisomers may be obtained by separating the mixture with high pressure liquid chromatography (HPLC). In particular, the HPLC separation may be carried out onto a reverse phase column, using a mixture of phosphate buffer, such as 10 mM $K_2HPO_4$ adjusted to pH 7.0 with 85% $H_3PO_4$, and an organic solvent as mobile phase, such as tetrahydrofuran or acetonitrile.

The starting material for the preparation of the new anthracycline glycosides is 4-demethoxy-3'-deamino-3'-aziridinyl-4'-methansulfonyl daunorubicin (II), and it is described in U.S. Pat. No. 5,532,218.

The invention further provides a pharmaceutical composition comprising an anthracycline glycoside of formula I in admixture with a pharmaceutically acceptable diluent or carrier. Conventional carriers and diluents may be used. The composition may be formulated and administered in conventional manner.

The compounds according to the invention are useful in methods of treatment of the human or animal body by therapy. They are useful as anti-tumor agents. They are useful in the treatment of leukemia and solid tumors, such as colon, colon-rectal, ovarian, mammary, prostate, lung, kidney and also melanoma tumors. A human can therefore be treated by a method comprising administering thereto a therapeutically effective amount of a compound of the invention. The condition of the human patient can thus be improved. The dosage to be given can be ascertained using known dosage ranges in the field of anthracyclines, modified by reference to the activity shown by the present compounds in in vitro and in vivo anti-tumor tests. Suitable dosages are generally in the range of 1 to 200 $mg/m^2$ body surface, preferably from 1 to 100 $mg/m^2$, depending on the nature and severity of the disease being treated and on the general condition of the patient. The compounds of formula I were tested and found active in vitro against a panel of murine and human tumor cell lines, and in vivo on disseminated P388/DX murine leukemia.

In vitro and in vivo Activity of Ia

On a panel of murine and human tumor cell lines, Ia presents high cytotoxicity as shown by $IC_{50}$ values of Tab. 1. The results of in vivo test of Ia on disseminated P388/DX murine leukemia are shown in Tab.2.

TABLE 1

In vitro cytotoxicity of Ia

| Cell Line[1] | Ia $IC^2_{50}$ ng/mL Mean ± SE |
|---|---|
| L1210[3] | 3.76 ± 0.13 |
| JURKAT[3] | 4.87 ± 0.7 |
| CEM[3] | 5.86 ± 0.4 |
| LoVo[4] | 20.3 ± 2 |

[1] Cells incubated with the compound for 1 h.
[2] 50% inhibitory concentration represents the mean ± SE from dose-response curves of at least two experiments
[3] Growth inhibition determined by counting surviving cells.
[4] Growth inhibition determined by SRB colorimetric assay.

TABLE 2

In vivo antitumor activity of Ia against disseminated P388/DX

| Compound | Dose[2] (mg/kg/day) | ILS %[3] | Tox[4] | LTS[5] |
|---|---|---|---|---|
| Ia | 2.9 | 80 | 0/20 | 0/20 |
|  | 3.8 | 102 | 4/17 | 0/17 |

[1]P388/DX Johnson leukemia cells ($10^5$/mouse) are injected IV on day 0.
[2]Treatment is given IV on day 1 after tumor transplantation (day 0). Ia was solubilized in [Cremophor ®/Ethanol = 6.5:3.5]/[normal saline] = 20/80 v/v
[3]Increase in life span:[(median survival time of treated mice/median survival time of controls) × 100] −100.
[4]Number of toxic deaths/number of mice.
[5]Long-term survivors (>60 days) at the end of the experiments The following example illustrates the invention.

EXAMPLE 1

13(R/S)-Dihydro-4-Demethoxy-3'-Deamino-3'-Aziridinyl-4'-Methansulfonyl Daunorubicin (Ia)

4-demethoxy-3'-deamino-3'-aziridinyl-4'-methansulfonyl daunorubicin (II, 600 mg, 1 mmol) were dissolved in methylene chloride (50 ml) and cooled at −70° C. The solution was added dropwise with a solution of sodium borohydride (120 mg, 3.2 mmol) dissolved in methanol (5 ml). After 15 minutes, acetone (10 ml) is added, than the reaction mixture is brought at room temperature, added with methylene chloride (500 ml) and washed with water (2×200 ml). The organic phase is separated, concentrated to smal volume and flash chromatographed on silica gel using a mixture of toluene and acetone (8:2 by volume). The fractions containing the title compound are pooled, concentrated to small volume and precipitated with a mixture of exane ethyl ether (85:5 by volume) to give 13(R/S)-dihydro-4-demethoxy-3'-deamino-3'-aziridinyl-4'-methansulfonyl daunorubicin (Ia, 400 mg).

TLC on Kieselgel Plate (Merck) using as eluent a mixture of toluene and acetone (80:20 by volume), $R_f$=0.3

$^1$H NMR (400 Mhz, CDCl$_3$) δ: 1.14, 1.23, 1.72 (m, CH$_2$CH$_2$ aziridine, Ia+Ib); 1.27 (d, J=6.3Hz, CH$_3$-13, Ib); 1.32 (d, J=6.3Hz, CH$_3$-13, Ia); 1.38 (d, J=6.5Hz, CH$_3$-5', Ia+Ib); 1.47 (ddd, J=2.6, 4.5, 12.5Hz, CH$_3$-3', Ia+Ib); 1.78 (m, H-2'ax, Ia+Ib; H-8ax, Ia); 1.87 (dd, J=4.1, 15.0Hz, H-8ax, Ib); 2.07 (dd, J=4.0, 13.4Hz, H-2'eq, Ia); 2.10 (dd, J=4.0, 13.4Hz, H-2'eq, Ib); 2.12 (d, J=7.8Hz, OH-13, Ia); 2.35 (ddd, J=1.7, 2.6, 15.0Hz, H-8eq, Ib); 2.40 (d, J=3.8Hz, OH-13, Ib); 2.54 (ddd, J=1.7, 2.6, 15.0Hz, H-8eq, Ia); 2.61 (d, J=19.1Hz, H-10ax, Ia); 2.65 (d, J=19.1Hz, H-10ax, Ib); 3.20 (dd, J=1.9, 19.1Hz, H-10eq, Ia+Ib); 3.21 (s, SO$_2$CH$_3$); 3.67 (m, CH-13, Ia); 3.82 (m, CH-13, Ib); 4.11 (m, H-5', Ia+Ib); 4.22 (s, OH-9, Ia); 4.36 (s, OH-9, Ib); 4.74 (m, H-4', Ia+Ib); 5.27 (dd, J=2.6, 4.4Hz, H-7, Ia); 5.29 (dd, J=2.6, 4.4Hz, H-7, Ib); 5.55 (d, J=3.8Hz, H-1', Ia+Ib); 7.84 (m, H-2+H-3, Ia+Ib); 8.36 (m, H-1+H-4, Ia+Ib); 13.38 (s, OH-11, Ia); 13.39 (s, OH-11, Ib); 13.59 (s, OH-6, Ia); !3.60 (s, OH-6, Ib).

FAB-MS (+) m/z: 604 [MH]$^+$

What is claimed is:

1. An anthracycline glycoside of formula I

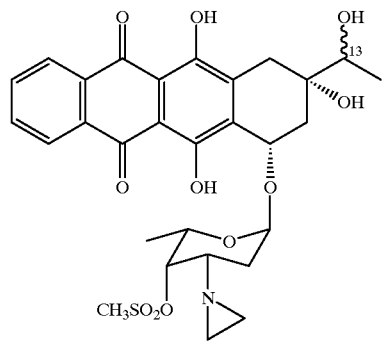

wherein the wavy line means that the hydroxy group at 13-position may be at α or β position, or a mixture thereof.

2. A compound according to claim 1 which is 4-demethoxy-13 (S/R) dihydro-3'-deamino-3'-aziridinyl-4'-methansulfonyl daunorubicin, 4-demethoxy-13(S) dihydro-3'-deamino-3'-aziridinyl-4'-methansulfonyl daunorubicin or 4-demethoxy-13(R) dihydro-3'-deamino-3'-aziridinyl-4'-methansulfonyl daunorubicin.

3. A compound according to claim 1 which is 4-demethoxy-13(S) dihydro-3'-deamino-3'-aziridinyl-4'-methansulfonyl daunorubicin.

4. A process for the preparation of an anthracycline glycoside of formula (I) as defined in claim 1, which process comprises reducing the anthracycline of the formula II

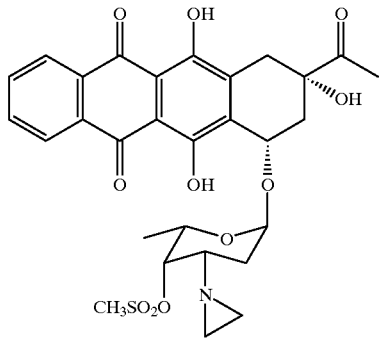

in presence of a reductive agent in a mixture of organic solvents, and, if desired and necessary, separating the resultant mixture of 13(R) and 13(S) compounds into the single diastereoisomer.

5. A process according to claim 4, in which the reductive agent is sodium borohydride.

6. A process according to claims 4, in which the reduction is carried out at a temperature below 50° C.

7. A process according to claims 6 in which the reduction is carried out at a temperature of −70° C.

8. A pharmaceutical composition comprising an anthracycline glycoside of formula I as defined in claim 1, and a pharmaceutically acceptable carrier or diluent.

9. A method of treating tumors, comprising administering to a patient in need thererof, a pharmaceutically effective amount of the anthracycline glycoside of claim 1.

10. The method of claim 9, wherein said tumor is selected from the group consisting of leukemia and a solid tumor.

* * * * *